United States Patent [19]

Taniguchi et al.

[11] 4,335,369
[45] Jun. 15, 1982

[54] OXYGEN SENSOR

[75] Inventors: Harutaka Taniguchi; Kenichi Hara; Hideo Shiraishi, all of Kawasaki, Japan

[73] Assignee: Fuji Electric Co., Ltd., Kanagawa, Japan

[21] Appl. No.: 194,242

[22] PCT Filed: Jul. 26, 1979

[86] PCT No.: PCT/JP79/00195
§ 371 Date: Mar. 14, 1980
§ 102(e) Date: Mar. 14, 1980

[30] Foreign Application Priority Data

Jul. 26, 1978 [JP] Japan ................................ 53/91203

[51] Int. Cl.$^3$ ............................................. H01L 7/00
[52] U.S. Cl. ..................................... 338/34; 338/229; 338/271
[58] Field of Search .................... 338/34, 13, 28, 30, 338/229, 271; 73/27 R; 422/98; 23/232 E; 324/65 R, 65 P

[56] References Cited

U.S. PATENT DOCUMENTS

| | | | |
|---|---|---|---|
| 4,007,435 | 2/1977 | Tien | 338/34 X |
| 4,033,169 | 7/1977 | Fujishiro et al. | 338/34 X |
| 4,130,797 | 12/1978 | Hattori et al. | 338/34 X |
| 4,206,173 | 6/1980 | Yamaguchi et al. | 338/34 X |

FOREIGN PATENT DOCUMENTS 48-70596 9/1973 Japan .
48-90294 11/1973 Japan .

Primary Examiner—C. L. Albritton

[57] ABSTRACT

An oxygen sensor in which a porous thick membrane (20) of transition-metal oxide and electrode metal thick membranes (14, 16) are provided on a ceramic base and these membranes are coated with a ceramic protective layer. The oxygen sensor in which the transition-metal oxide and the electrode metal are constructed in the forms of thick membranes and the protective layer is formed by plasma spray coating is mechanically tough and permits the gas to diffuse rapidly into the porous structure with rapid variation in the electric resistance depending on an oxygen partial pressure in the gas. Accordingly, the oxygen sensor may be conveniently used for detecting an oxygen content in the waste gas from automobiles.

9 Claims, 7 Drawing Figures

OXYGEN SENSOR

TECHNICAL FIELD

This invention relates to an oxygen sensor for detecting oxygen content in a waste gas from automobiles or the like which has superior mechanical toughness and sensitivity and comprises a ceramic base which is provided with a porous thick membrane of transition-metal oxide and thick membranes of electrode metal and these thick membranes are coated with a protective ceramic layer.

BACKGROUND OF THE INVENTION

In a tertiary catalyst system empolyed as one of measures for public nuisance of automobile waste gas, an air/fuel ratio is controlled within a very narrow range of the equivalence point and an oxygen content after combustion is detected as an oxygen partial pressure by means of an oxygen sensor and then the detected signal is fed back to a control system of a fuel supplying unit. Therefore, the oxygen sensor is required to respond quickly to the oxygen partial pressure in the waste gas emitted from a heat engine of automobiles or the like. Namely, the oxygen sensor is required to exhibit a quick response time at least in the same degree as that shown by transmission property between a heat engine and a fluid medium with an efficient contact of the waste gas with an oxide. In the oxygen sensor detecting a change in the oxygen partial pressure of the ambient atmosphere as a change in the electric resistance, a transition-metal oxide is conventionally used for the material. The change in the electric resistance of the transition-metal oxide is caused due to variation in the stoichiometry of the oxide crystal and this change in the stoichiometry is induced through a possible contact with an oxygen in the waste gas. The response characteristic of the oxygen sensor is nothing but the response characteristic of the change in the electric resistance and the speed of the response of the stoichiometry or that of the change in the electric resistance of the oxide crystal is directly influenced by the contact efficiency between the waste gas and the oxide crystal, or the diffusion rate of the waste gas into the crystal. In general, the sensor element consisting essentially of such transition-metal oxide is formed into a disc shape by mixing an oxide with an organic binder solution, forming the mixture into green sheets by a doctor blade and then holding electrodes between the sheets for firing. Since, however, the element alone is mechanically weak, it must be assembled into a ceramic or metal support for practical use. Further, there is another disadvantage that the speed of the response of the oxygen sensor through the change in resistance of the transition-metal oxide is inferior to the conventional sensor wherein a change in the electromotive force of the zirconium oxide is utilized.

DISCLOSURE OF THE INVENTION

An object of the present invention is to provide an oxygen sensor in which an element per se comprising an oxide and a connecting lead wire has a mechanically strong structure with superior response characteristic. This object may be performed by an oxygen sensor in which a porous thick membrane of transition-metal oxide having a thickness of 50 to 100 μm and electrode metal thick membranes divided into two parts in contact with the porous thick membrane are arranged on a ceramic base and all free surfaces of the thick membrane of transition-metal oxide and at least a part of free surfaces of electrode metal thick membranes are covered with a ceramic protective layer. By this arrangement, there may be brought such the advantages that the waste gas from automobiles or the like is diffused well rapidly into the oxide crystal, that the mechanical stress due to vibration in the heat engine is minimized since the oxide in the form of the membrane reduced the mass and weight and that generation of heat shock or heat cycle through start, stop, acceleration or deceleration of the operation produce a low thermal gradient because of the oxide in the form of membrane, resulting in increase of resistance to the spalling.

BRIEF DESCRIPTION OF THE DRAWINGS

The drawings illustrate several preferable embodiments of the oxygen sensor according to the invention, in which.

THE MOST PREFERRED EMBODIMENTS OF THE INVENTION

Figure 1:
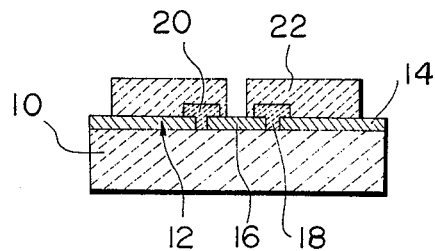
FIG. 1 is a sectional view of the oxygen sensor of one embodiment according to the invention.

In FIG. 1, the reference numeral 10 stands for a disc which consists of 95% aluminum oxide and is, when desired, sandblasted to form the surfaces in 3 to 4 S roughness. The disc 10 is defatted under the supersonic function before a platinum electrode 12 is fired onto the surface of the disc. The platinum electrode 12 is divided into concentric electrodes 14 and 16 which are spaced apart each other in a distance 18 of approximately 100 μm. When the electrode is formed, platinum paste is primarily printed in a suitable pattern by means of a printing machine with a stainless screen of not less than 325 mesh. The resulting print is left to stand at 200° C. for approximately one hour to evaporate the solvent and to heat-cure the binder for subsequent heating at 500° C. for two hours to completely fire the binder and thereafter is heated in an constantly increasing temperature up to 1300° C. for baking to obtain a platinum membrane of porous body 12 having a thickness of approximately 8 μm. Then, an oxide membrane 20 is formed. As the oxide, for example, titanium dioxide may be used. The titanium dioxide is analogous to the platinum paste of the composition as shown, for example, in Table 1.

TABLE 1

| | |
|---|---|
| Titanium Dioxide Material | 60 wt. % |
| Binder-(Alkyd Melamine Resin) | 20 wt. % |
| Solvent (Diethylene Glycol Monoethyl Ether) | 20 wt. % |

To the titanium dioxide is added a doping material (when desired). These materials are blended and uniformly dispersed by means of the supersonic. For adjustment of the viscosity, some nitrocellulose may be added together with the binder. For further uniform dispersion, a pot containing the paste is rotated before the paste is printed in a width of 400–500 μm by means of a convenient printing machine with a stainless screen of 60 μm thickness. In particular, since the titanium oxide paste is liable to entrap air-bubbles the paste is printed, left stationarily and dried in several times.

An application of the paste in a small amount ensures a sufficient deaeration and a uniform thickness of the print. If the thick titanium dioxide membrane contains the air-bubbles, then an electric short-circuiting occurs. Accordingly, the amount for one application is of the order of 15 μm which enables the air-bubbles to escape only by leaving to stand with the rapid drying but without causing non-uniformity of thickness due to sag of the paste. The paste is left to stand for about 30 minutes and dried at the temperature of 200° C. for one hour. The printing number of times may be controlled depending on the thickness after baking. The thickness of the oxide thick membrane 20 is preferably small as hereinbefore described altho if too thin the sintering proceeds to produce poor porosity which disturbs sufficient diffusion of the waste gas. Thus, the thickness may preferably be adjusted between 50 μm and 100 μm. The conventional green sheet technique could not reduce the thickness to the degree of less than 200 μm, whereas the present method ensures the sufficiently thin thickness. The firing may be performed through the same firing procedure of the binder as in the platinum electrode at the temperatures of from 1,100° to 1,300° C. As a result, the titanium dioxide thick membrane 20 thus obtained has a sufficient porosity of a density of 70 to 80% in theoretical value with sufficiently small thickness and short time for replacing the waste gas, resulting in improved speed of the response. The titanium dioxide thick membrane 20 is coated with a protective layer 22 which is formed by the plasma spray coating of magnesia spinel. Namely, the sample is placed on a turn-table for preheating and then the spinel powder is sprayed through a plasma gun. The sprayed membrane has a thickness of 50–100 μm and is porous. The platinum thick membrane 12 is also porous and hence a sufficient bonding strength with the plasma sprayed membrane or the protective layer 22 may be obtained. The bonding strength thus obtained is greater than that between the plasma-sprayed membrane 22 and the titanium dioxide membrane 20. Accordingly, the width of the titanium dioxide membrane 20 over the platinum electrode 12 may be relatively small and a possibly large contacting area of the plasma-sprayed membrane 22 with the platinum electrode 12 ensures a more toughened structure. Since the insufficient strength of the alumina base 10 is liable to suffer damage during the spraying operation, the base 10 should have a sufficient strength for sintering. The protective layer 22 prevents the platinum thick membrane 12 and the titanium dioxide thick membrane 20 from generating erosion on account of a waste gas and also serves as a thermal insulating protective layer for alleviating a thermal strain caused by rapid heating or cooling of the titanium dioxide membrane 20 with the waste gas since the spinel membrane has a half thermal conductivity of alumina. In the structure as shown in FIG. 1 the thin platinum electrode 12 has a small sectional area, so that a whole distance of the gap 18 between the electrodes is extended as long as possible in order to reduce the resistance of the whole element, and the space of the gap is possibly minimized for example approximately 100 μm, when the printing technique permits.

Figure 2:
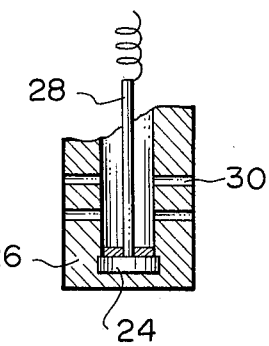
FIG. 2 is a sectional view showing a practically applied position of the sensor of FIG. 1.

FIG. 2 shows the oxygen sensor element in a practically applied position, wherein an oxygen sensor element 24 if fixed to a bottom of a housing 26 and one platinum electrode 14 of FIG. 1 constituting the element 24 is connected to a housing 26, while the other electrode 16 is connected to a lead rod 28 inserted into a middle portion of the housing 26. The waste gas reaches the surface of the sensor element 24 through holes 30 opened in the side walls of the housing 26.

Figure 3:
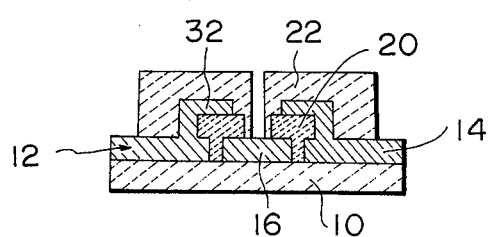
FIG. 3 is a sectional view of the oxygen sensor of another embodiment.

FIG. 3 shows another embodiment wherein the titanium dioxide thick membrane 20 is held between the electrodes 14 and 16 on the base 10 of an aluminum oxide disc. In this arrangement as different from that shown in FIG. 1, the titanium dioxide membrane 20 is contacted with the electrode not only from the left and right sides but also from the top and bottom sides as well as from the diagonal direction, so that all these parts may be contributed to the conductivity, thereby reducing the total resistivity of the whole element. It will be well appreciated from FIG. 3 that a third layer of platinum electrode 32 is overlayed and fired onto the first layer of platinum electrodes 14, 16 and the second layer of titanium oxide thick membrane 20. In this arrangement, the second and third layers are simultaneously fired, because the application of the third layer of platinum paste after firing of the second layer of titanium oxide thick layer 20 allows the platinum paste to penetrate into the porous titanium oxide thick layer 20 with undesired risk of short-circuiting. In the simultaneous firing operation the drying process for the second layer of titanium oxide thick membrane is particularly necessitated. Namely, an insufficient drying allows the platinum paste for the third layer to penetrate into the titanium dioxide paste layer. When the drying operation is effected at 200° C. for approximately one hour, the resin in the paste is sufficiently heat-cured and prevented from reacting with a solvent for dissolusion. Thus, the penetration of the third layer of platinum paste may be perfectly avoided. The second and the third layers after successively applied and dried are simultaneously fired. The thickness of the titanium dioxide thick layer 20 is adjusted in the range of 50 to 100 μm and the protective layer 22 is applied by means of spray as similar to the embodiment of FIG. 1. In this embodiment, the contacting area of the protective layer 22 with the platinum electrode 12 is enlarged broader than that of the enbodiment of FIG. 1 with increment of the mechanical strength.

Figure 4:
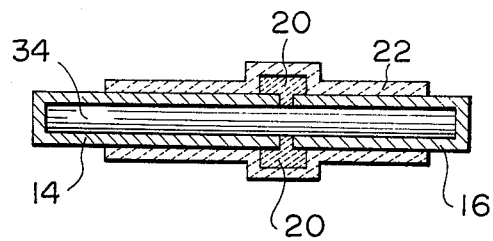
FIGS. 4 and 5 are sectional views of the oxygen sensor of different embodiments with a round rod used for the base.
Figure 5:
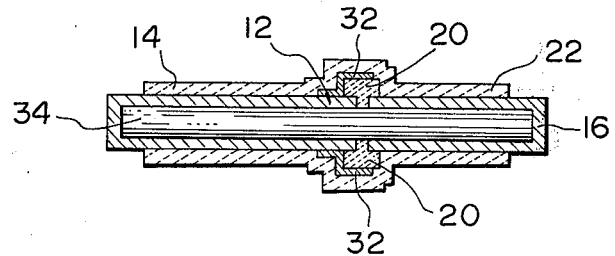

FIGS. 4 and 5 show another embodiments of the invention wherein the numeral references represent the same elements as shown in FIGS. 1 and 3. In these embodiments a ceramic round rod 34 is employed as the base for the thick membranes which are printed on the curved surface of the rod 34. In this arrangement, the connecting lead wire may also be made into a thick membrane free of other lead wires which are required in the embodiment of FIG. 2.

Figure 6:
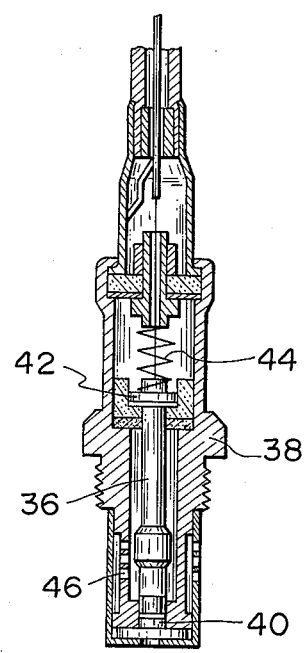
FIG. 6 is a sectional view of the oxygen sensor showing a practically applied position of the embodiment as shown in FIG. 4 or 5.

FIG. 6 shows a practically applied position of the embodiment, wherein the element 36 is held between a lower contacting terminal 40 and an upper contacting terminal 42 within the housing 38 and particularly the contacting terminal 42 is made into contact with the electrodes 14 and 16 under the pressure of a spring 44. It will be appreciated that these contacting parts are located at the upper and lower sections which have little direct contact with the waste gas to be introduced through an air hole 46. The embodiment of FIG. 4 corresponds to that of FIG. 1 with a single layer of platinum electrode, while the embodiment of FIG. 5 corresponds to that of FIG. 3 with two layers of platinum electrodes.

Figure 7:
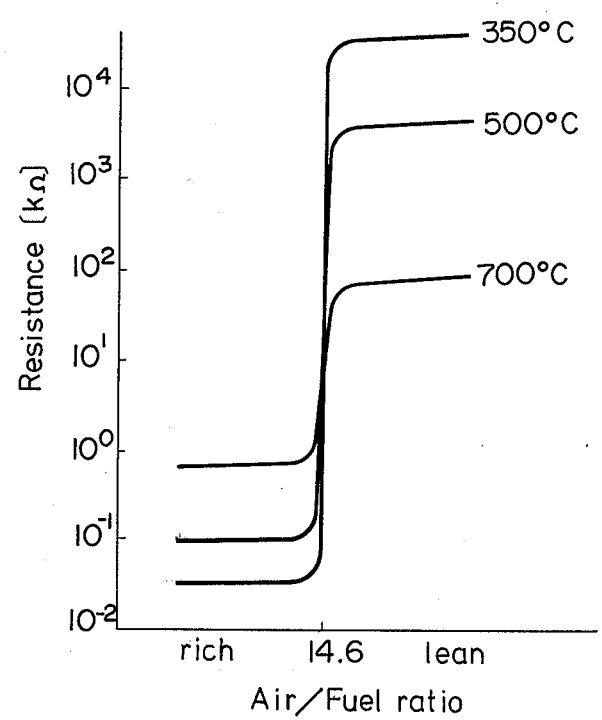
FIG. 7 is a graphical diagram showing an air/fuel ratio of resistivity of the oxygen sensor according to the invention.

FIG. 7 shows an air/fuel ratio (A/F) of the titanium dioxide oxygen sensor according to the invention. In the tertiary catalyst system, the highest conversion efficiency of redox characteristics is desired to exist in the proximity of A/F=14.6, for which reason the oxygen sensor should be used to feed-back the signal for adjusting the value of A/F to approximately 14.6. The temperature of the waste gas of automobiles is usually in the range of 350° to 900° C. among which the feed back temperature is in the range of about 350° to 700° C., so that the resistance in this temperature range is desired to change rapidly at A/F of 14.6. The characteristic in FIG. 7 shows that the oxygen sensor according to the invention satisfies this requirement. In order to evaluate the response characteristic of the oxygen sensor in the actual vehicle, the response speed or the frequency response characteristic of the oxygen sensor when a rich gas and a lean gas are alternately supplied to the oxygen sensor in repetition. When the titanium dioxide oxygen sensor according to the invention is used to convert the rich gas of a flow rate of 3.0 ι/min. and A/F of 0.5 into the lean gas of A/F of 1.5 at the resistance of 330 Ω, the response characteristic is of not less than 2 Hz in the range of 350° to 700° C. is about two times of the response characteristic of the titanium dioxide oxygen sensor of disc type.

In the examples as hereinbefore described, the titanium oxide is employed as an oxide altho other transition-metal oxides such as the cobalt oxide may be also applied in the oxygen sensor. Further, a platinum as an electrode metal may be applied by means of spattering process, ion-plating process or the like without using screen-printing process and metals other than platinum may also be employed for the electrode.

In the oxygen sensor according to the invention, either the resistor or the electrode are made of thick membranes so that consumption of the materials is extremely low, resulting in reduction of the material cost. Further combination of the thick membrane with the spray-coating ensures an increment of the mechanical strength with sufficient practical durability for providing an oxygen sensor of excellent response characteristic.

Industrial Applicability of The Invention

As hereinbefore fully described, the oxygen sensor according to the invention has a sufficient endurance to the mechanical stress and a high speed of response, so that it may be advantageously utilized to control the waste gas from the heat engine, especially from automobile with significant effect on the measures for public nuisance.

We claim:

1. An oxygen sensor for detecting a change of an oxygen partial pressure in an ambient atmosphere through a change of an electric resistance of a transition-metal oxide, characterized in that a porous thick membrane of transition-metal oxide having a thickness of 50 to 100 μm and electrode metal thick membranes divided into two parts in contact with said porous thick membrane are arranged on a ceramic base and all free surfaces of said thick membrane of transition-metal oxide and at least part of free surfaces of said electrode metal thick membranes are coated with a ceramic protective layer.

2. An oxygen sensor as claimed in claim 1, wherein the ceramic protective layer is applied by spray-coating.

3. An oxygen sensor as claimed in claim 1, wherein the thick membrane of transition-metal oxide consists of a titanium dioxide.

4. An oxygen sensor as claimed in claim 1, wherein the electrode metal thick membrane consists of a platinum.

5. An oxygen sensor as claimed in claim 2, wherein the ceramic protective layer consists of a magnesia spinel.

6. An oxygen sensor as claimed in claim 1, wherein the thick membrane of transition-metal oxide and the electrode metal thick membrane are applied by screen-printing of powdery pastes before firing.

7. An oxygen sensor as claimed in any of claims 1-5, wherein the ceramic base is made of a round rod.

8. An oxygen sensor as claimed in any of claims 1-5, wherein a second electrode metal thick membrane is coated over the thick membrane of transition-metal oxide and one of the electrode metal thick membranes provided on the ceramic base for covering at least part of the surfaces of the thick membranes.

9. An oxygen sensor as claimed in claim 8, wherein the second electrode metal thick membrane and the thick membrane of transition-metal oxide are fired simultaneously.

* * * * *